United States Patent [19]

Gama

[11] 4,330,275

[45] May 18, 1982

[54] ARTICULATOR FOR MODELS OF DENTAL ARCHES

[76] Inventor: José M. Gama, Praca de Bandeiro 200, Belo Horizonte, Minas Gerais, Brazil

[21] Appl. No.: 184,130

[22] Filed: Sep. 4, 1980

[30] Foreign Application Priority Data

Dec. 9, 1979 [BR] Brazil .............................. 7905829[U]

[51] Int. Cl.³ .............................................. A61C 11/00
[52] U.S. Cl. ........................................ 433/57; 433/60; 433/54
[58] Field of Search ........................ 433/57, 59, 60, 54

[56] References Cited

U.S. PATENT DOCUMENTS

| | | | |
|---|---|---|---|
| 537,812 | 4/1895 | Bragg | 433/60 |
| 1,684,393 | 9/1928 | Gysi | 433/60 |
| 2,909,837 | 10/1959 | Gerber | 433/57 |
| 3,769,708 | 11/1973 | Guichet | 433/57 |

FOREIGN PATENT DOCUMENTS

| | | | |
|---|---|---|---|
| 433839 | 8/1935 | United Kingdom | 433/60 |
| 742122 | 12/1955 | United Kingdom | 433/60 |

Primary Examiner—Robert Peshock
Assistant Examiner—John J. Wilson
Attorney, Agent, or Firm—Orville N. Greene

[57] ABSTRACT

The articulator is the type which has an upper part with a horizontal branch and a lower part with a horizontal branch below and substantially parallel to the upper branch. The upper part has a pair of spaced wings connected to the rear of the upper branch and angling upwardly at a small angle therefrom as well as an adjustable incisor pin extending downwardly from the front end thereof. The lower branch has a pair of spaced articulator pins extending upwardly into slots in the wings of the upper part as well as an incisal tray angling downwardly from the front end to receive the incisal pin. Thus the upper part is supported in the lower part as a tripod with a relatively low center of gravity. A mold is provided to be connected to the articulator.

3 Claims, 9 Drawing Figures

ARTICULATOR FOR MODELS OF DENTAL ARCHES

This invention relates to improvements in the articulator for models of dental arches.

Articulators are used in prosthodontics, allowing the prosthodontist to simulate such articulations as may be obtained from the dental arch of the patient. Accordingly, it is possible to make in the articulator all of the adjustments, inserts and modifications in the dental supplies to be acquired by the patient.

The improved articulator of the present invention has some of the characteristics of kindred devices, particularly with regard to articulation, fixation of the opening and dampening of movements.

Among the objects of the invention is to provide an articulator with an upper part which has a low center of gravity and which is able to make certain lateral movements with respect to the lower part without disengagement therefrom.

Further objects and advantages of the invention will be apparent from the reading of the subjoined specification and claims and from a consideration of the accompanying drawing showing an embodiment of the invention.

The articulator comprises two principal parts, the upper piece having a horizontal branch 1 and two spaced wings 9, and a lower piece. The lower piece contains a horizontal branch 2 and two upright members 3 each ending in an articulator pin 11 having a bulbous end portion which enter into the respective slots 18 of the articulator wings 9 and slots 18 therein are inclined upwardly with respect to the horizontal branch 1 thereof, are widely spaced and are connected to the main body 1 of the upper piece by arms 16. The upward inclination of the wings 9 can vary up to around 60°. The upright members or branches 3 of lower piece 2 are connected to the horizontal branch of the lower piece by similar arms 31. In the front portion of horizontal branch 2 an incisal tray 10 is provided having an inclination as shown. The inclination which is shown at an angle of about 30° can vary between about 5° and 60°.

Figure 1:
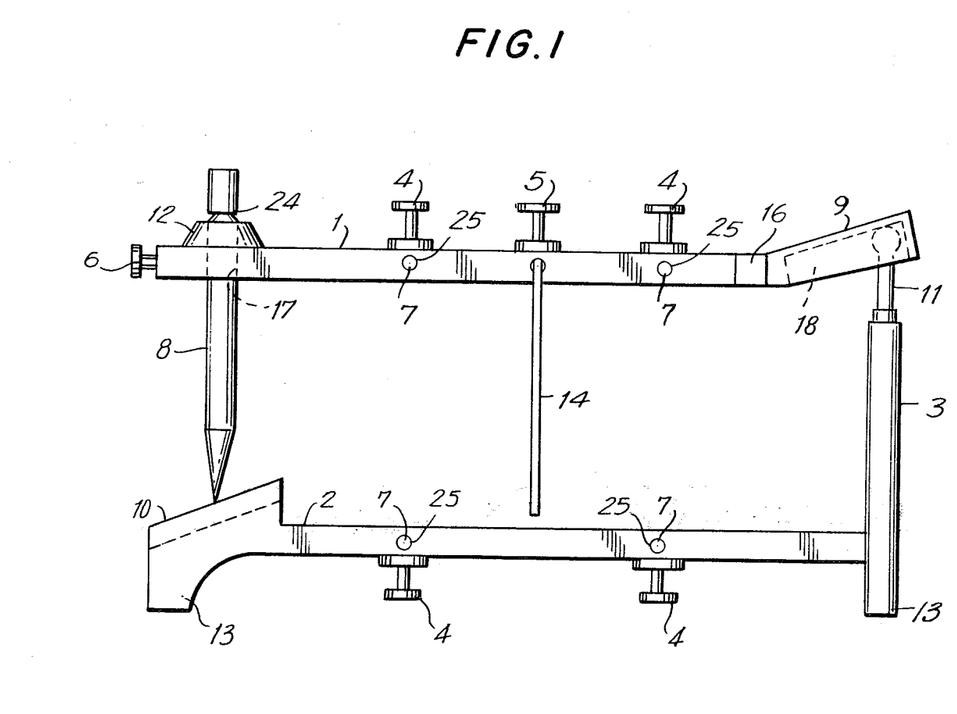
FIG. 1 is a side view of the improved articulator.

The horizontal branches 1 and 2 have lateral holes 25, three on each side of the upper horizontal branch and two each side of the lower horizontal branch 2 (FIG. 1). The upper holes 25 hold the retaining pins 7 (FIGS. 1, 2 and 3) and the longer portion of the connecting member 14. The lower holes 25 hold only the retaining pins 7 (FIGS. 1 and 4); perpendicular to these holes and coincidental therewith, the holding screws 4 for the retaining pins 7 and the holding and adjusting screws 5 for the connecting member 14 are provided.

The parallelism between the horizontal portion of pieces 1 and 2 of the articulator is maintained, in the back part, by the articulator pins 11 positioned within the articular slots 18 and, in the front part, by the incisal pin 8 resting on the incisal tray 10 forming a tripod. Such pin 8, which is adjusted and held in place in the hole 17 by the holding and adjusting screw 6 is stabilized with the aid of the stabilizing tapered member 12 (FIG. 1).

The feet 13 of the articulator are three in number and of such height as to allow free operation of the holding screws 4 of the retaining pins 7 of the lower piece. These feet 13 are positioned on the lower horizontal piece 2 (FIG. 1).

The articular wings 9 consists of a ceiling 23 and four walls 19, 20, 21 and 22 which form the articular slots 18 (FIG. 3) in a novel way.

The internal walls 19 (included for merely aesthetical reasons) can be dispensed with with no impairment of the motion of the articulator and at the same time maintaining the required angularities any articulator must have. The motions of the articulator pins 11 are directed with the aid of the ceilings 23 and the outer walls 20, 21 and 22.

The outer walls 20 guide the movements of projection and retroprojection of the upper piece of the articulator on the articulator pins 11 and maintain such movements perfectly aligned by avoiding side movements of the upper piece, which are undesirable during said projection and retroprojection. The side movements take place when, resting in one of the angles formed by the back walls 21 and the external walls 20, a first articular pin 11 pivots on its axis while the second articular pin 11 on the opposite side moves frontward, downward and inward resting simply on the ceiling 23 of the articular slot 18 and undergoing no side friction. That condition makes the above described movement much smoother than the common movement. The important point here is that this has been attained thanks to the entirely new dimensions of the articulator which have been computed for this specific purpose.

The front walls 22 function as a joining member between the articular wings 9 and the arms 16 which in turn, joins them to the upper horizontal branch 1 of the articulator.

The ceilings 23 and the outer walls 20 and back wall 21, together with the incisal pin 8 and the articular pins 11 when they are in their places are what determine the initial position of the articulator in use.

Figure 2:
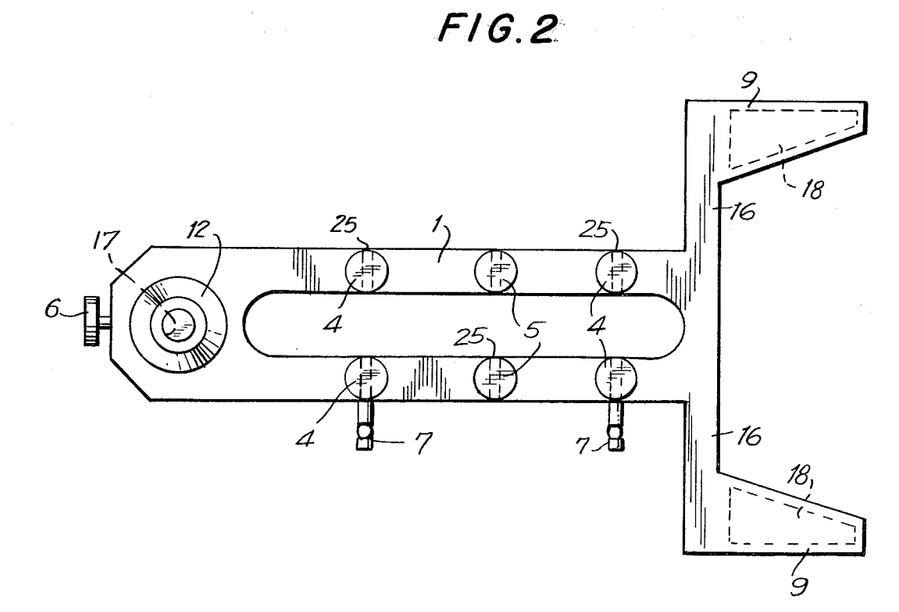
FIG. 2 is a plan view of the top surface of the upper piece of the articulator.
Figure 3:
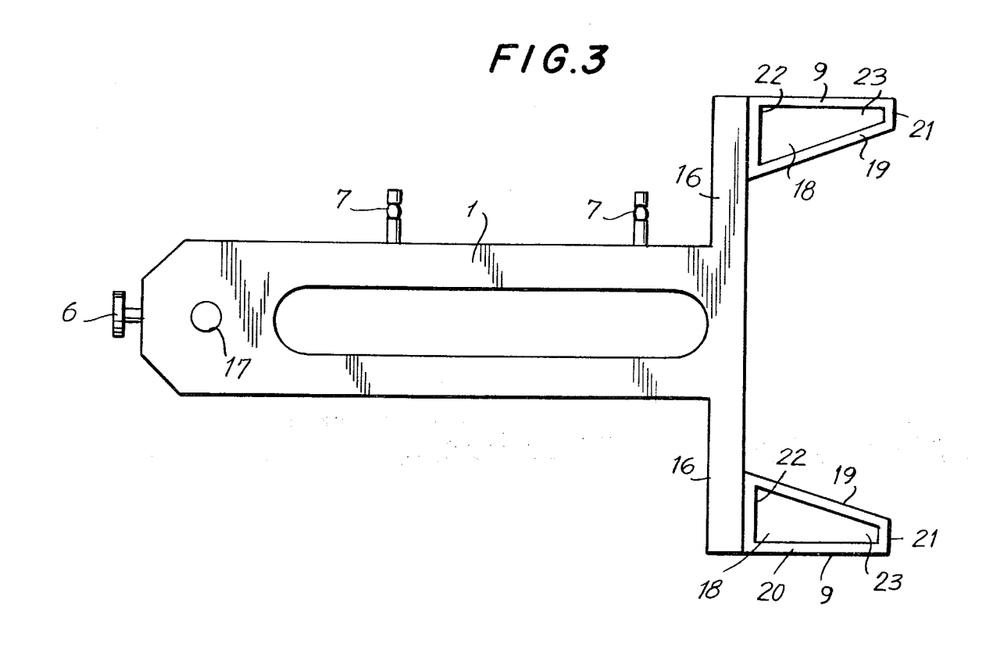
FIG. 3 is a plan view of the bottom surface of the upper piece of the articulator.
Figure 4:
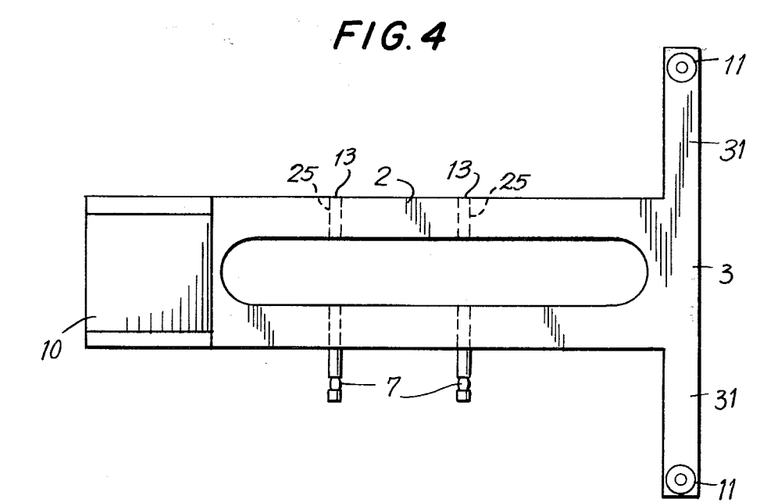
FIG. 4 is a plan view of the top surface of the lower piece of the articulator.

The articular wings 9 have been positioned in such a way as to impart novel properties to the articulator; for instance, the arms 16 that connect the articulator wings 9 to the horizontal branch 1 of the upper piece in this articulator are located in the front and lower part (wall 22) and not in the back and higher part (wall 21) of the articulator wings 9 (FIGS. 1, 2, and 3).

This transformation is similar to transforming a high-winged airplane into a low-winged one, thus providing the articulator with enhanced streamlining properties and smooth and safe movements.

The change of the position of the arms 16 to the front and lower part of the articular wings 9 changes the center of gravity of the piece to a much lower and more central location, which provides much greater stability to the articulator.

The retaining pins 7 (FIGS. 1 to 4), hold the plaster and feature three outstanding operating characteristics.

a. As the holes 25 that hold the retaining pins are parallel to each other, such pins, when connected in pairs, higher or lower pairs, or even pairs of higher and lower pins in conjunction, are easily removable when pulled sideways.

b. They have retaining means for holding the plaster, which enable removal of the pins in pairs.

c. They are further provided with a stop, which with the aid of the holding screws of the retaining pins 4, are maintained in their correct positions. On that account, on being removed, the pins can later be put back exactly in their old positions and only in such positions.

The incisal pin 8 is provided with a slot 24 in its upper part which determines, when such slot is aligned with the upper part of the stabilizing taper 12, the parallelism of the horizontal branches 1 and 2 of the articulator when the articulating pins 11 are positioned within the articular slot 18 (FIG. 1).

Figure 5:
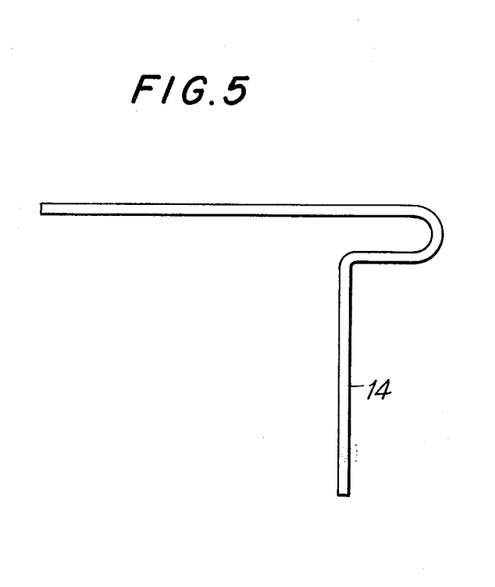
FIG. 5 is a detail view of the member for connecting the articulator to the special holder.
Figure 6:
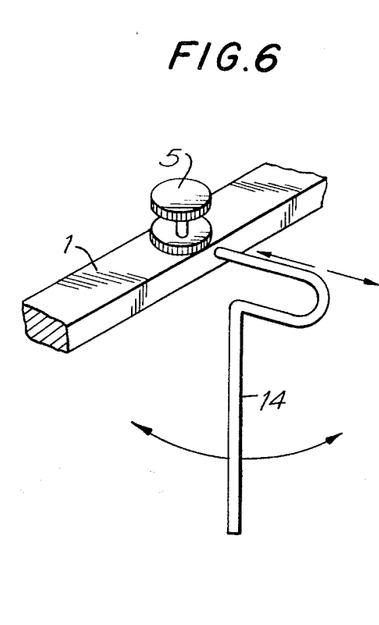
FIG. 6 is a view illustrating the movements of the connecting member.

The connecting member 14 (FIG. 5) consists of a steel wire bent into an "L" and its length has been designed so as to provide better support for the fingers when making the movements with the connecting member, which makes things handier for the operation, also in removing the plaster. As its name indicates, it is the member for the connection of the articulator with the special moulder. Its elongated portion fits into the central and lateral hole of the horizontal branch 1 of the upper piece of the articulator and the shorter portion into the special moulder, when positioned. The connecting member 14 has two movements, one like that of a pendulum and the other sideways, as the arrows in FIG. 6 show.

Comparatively speaking as regards stability, it is like changing the high center of gravity of a "Kombi"-type utility van to a low center of gravity like that of a "COPERSUCAR" racing car.

Figure 7:
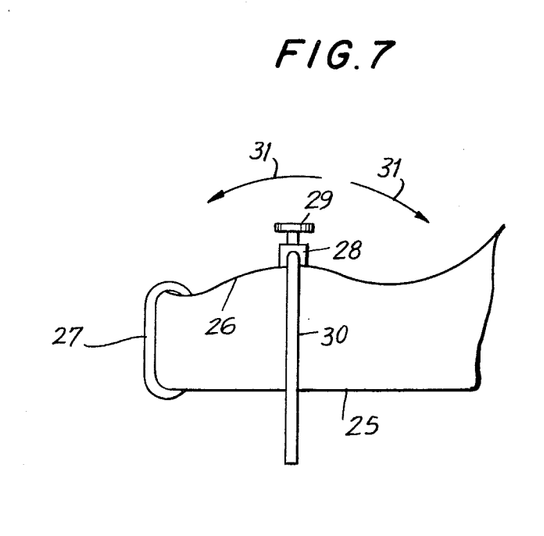
FIG. 7 is a side elevational view of the molder.
Figure 8:
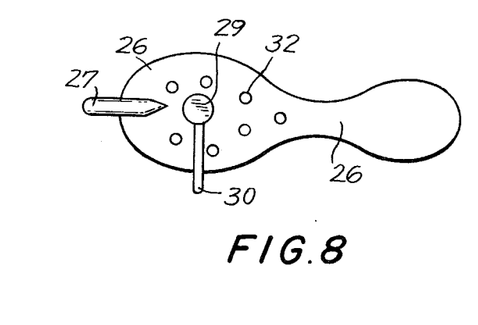
FIG. 8 is a plan view of the molder.
Figure 9:
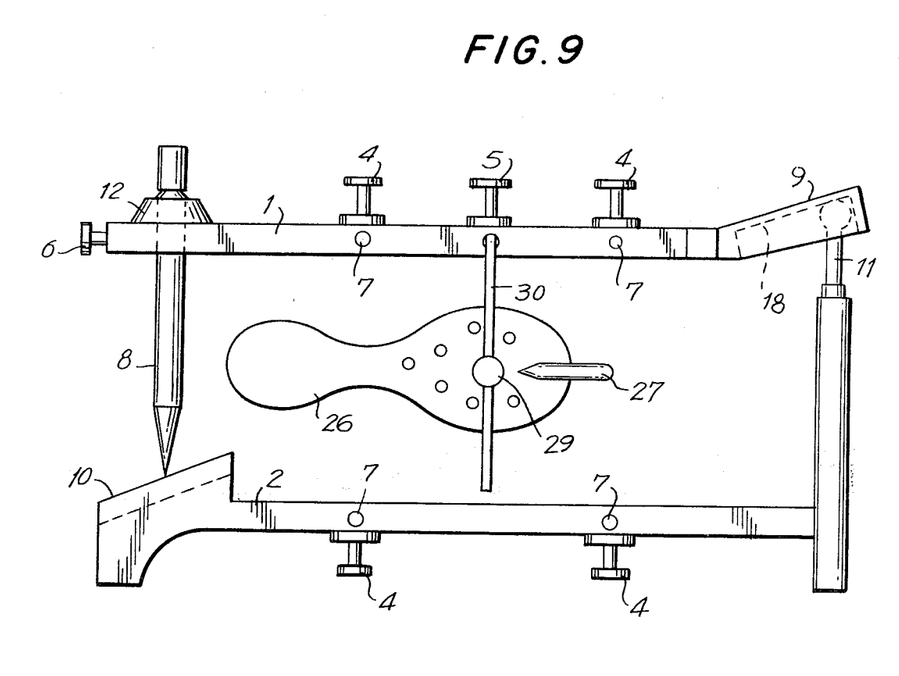
FIG. 9 is a side view of the articulator with the molder attached.

The improved moulder shown in FIGS. 7 and 8 is capable of simultaneously making both the upper and lower casts of the articulated dental arches and, unlike all other moulders, it can transfer such position and casting directly to the articulator, thus becoming an integral part of the articulator, with which it forms a single aggregate.

The new moulder consists of two wings 25 and 26 side by side, with enough space between them to contain the teeth and the desired casting material. The two wings which are slightly curved in keeping with the dental arches are joined together at the back by a fine but sufficiently rigid arch 27. The wings 25 and 26 are perforated to provide for the holding of the moulding or casting material.

The outer wing 26 contains the connecting assembly 28 with the connecting member 30 and such wing extends to a limit beyond that determined by the internal wing, so as to form a convexity into the moulder. Said extension of the wing 26 forms the handle of the moulder.

The connecting assembly 28 has two drillings or perforations:

a—One vertical perforation which holds the shorter portion of the connecting member 30 of the articulator to the moulder.

b—One horizontal perforation that holds the retaining and adjusting screw 29 of the connecting member.

When the connecting member 30 is fitted into the improved moulder, the latter can make the movements shown in FIGS. 7 and 8:

a—Vertically so that it can be positioned at the desired height.

b—Rotatively, around the axes of the shorter arm of the connecting member 30 so that it can be positioned relative to the dental arch.

I claim:

1. In an improved articulator for models of dental arches of the type having an upper part and a lower part with similar branches which are substantially horizontal and parallel to each other and articulating means connecting the parts, the improved articulator means comprising a pair of spaced articular wings extending upwardly at a slight angle from the rear of the horizontal branch of the upper part, a pair of arms extending laterally from said branch for connecting said arms to said horizontal branch, said arms being connected to said respective wings at the front and lower part of the latter, each of said wings having a slot therein which includes a rear wall and a wall which is exterior with respect to the horizontal branch, the front portion of the horizontal branch of said upper portion containing means for adjustable holding an incisal pin, an incisal pin in the latter, the lower part of said articulator containing a pair of uprights mounted thereon to extend upwardly to a region adjacent the wings of said upper part, a pair of articulator pins at the end of said uprights fitting into the respective slots of said wings and each being retained within the rear and external walls of its respective wing, the front portion of the horizontal branch of said lower part containing an incisal tray sloping downwardly at a small angle away from the horizontal branch, whereby said upper part is articulatingly supported on the lower part as a tripod with a low center of gravity.

2. The articulator as claimed in claim 1 comprising a connecting member consisting of a steel wire bent to the shape of an "L", the branch of said upper part containing an orifice to receive one leg of the "L".

3. In an improved articulator for models of dental arches of the type having an upper part and a lower part with similar branches which are substantially horizontal and parallel to each other and articulating means connecting the parts, the improved articulator means comprising a pair of spaced articular wings extending upwardly at a slight angle from the rear of the horizontal branch of the upper part, said pair of articular wings being connected to the horizontal branch by suitable arms extending laterally from said branch, each of said wings having a slot therein which includes a rear wall and a wall which is exterior with respect to the horizontal branch, the front portion of the horizontal branch of said upper portion containing means for adjustable holding an incisal pin, an incisal pin in the latter, the lower part of said articulator containing a pair of uprights mounted thereon to extend upwardly to a region adjacent the wings of said upper part, a pair of articular pins at the end of said uprights fitting into the respective slots of said wings and each being retained within the rear and external walls of its respective wing, the front portion of the horizontal branch of said lower part containing an incisal tray sloping downwardly at a small angle away from the horizontal branch, whereby said upper part is articulatingly supported on the lower part as a tripod with a low center of gravity, said upper and lower branches containing transverse openings adapted to receive retaining pins, retaining pins in said transversal openings, and a plurality of screw means, one associated with each transverse opening adapted to fix the position of the retaining pin in its transverse opening.

* * * * *